(12) United States Patent
Tuan et al.

(10) Patent No.: US 10,471,176 B2
(45) Date of Patent: Nov. 12, 2019

(54) COMPOSITION MATERIAL AND METHOD FOR FREE FORMING BONE SUBSTITUTE

(71) Applicant: National Taiwan University, Taipei (TW)

(72) Inventors: Wei-Hsing Tuan, Taipei (TW); Pei-Yi Hsu, Taipei (TW); Hui-Lan Chen, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/920,470

(22) Filed: Mar. 14, 2018

(65) Prior Publication Data

US 2018/0264168 A1 Sep. 20, 2018

Related U.S. Application Data

(60) Provisional application No. 62/470,897, filed on Mar. 14, 2017.

(51) Int. Cl.

| | |
|---|---|
| *A61L 27/12* | (2006.01) |
| *A61L 27/02* | (2006.01) |
| *A61L 27/58* | (2006.01) |
| *A61L 27/18* | (2006.01) |
| *A61L 27/46* | (2006.01) |
| *A61L 27/56* | (2006.01) |
| *B33Y 10/00* | (2015.01) |
| *B33Y 70/00* | (2015.01) |
| *B33Y 80/00* | (2015.01) |

(52) U.S. Cl.
CPC .............. *A61L 27/12* (2013.01); *A61L 27/025* (2013.01); *A61L 27/18* (2013.01); *A61L 27/46* (2013.01); *A61L 27/56* (2013.01); *A61L 27/58* (2013.01); *B33Y 10/00* (2014.12); *B33Y 70/00* (2014.12); *B33Y 80/00* (2014.12); *A61L 2430/02* (2013.01)

(58) Field of Classification Search
CPC .... A61L 27/18; A61L 2430/02; A61L 27/025; A61L 27/58; A61L 27/12; A61L 27/40; A61L 27/3847; A61L 27/56; B33Y 10/00; B33Y 70/00; B33Y 80/00
See application file for complete search history.

(56) References Cited

U.S. PATENT DOCUMENTS

| 4,963,145 A | 10/1990 | Takagi et al. |
| 2011/0052660 A1 | 3/2011 | Yang et al. |
| 2014/0128975 A1 | 5/2014 | Wang et al. |

FOREIGN PATENT DOCUMENTS

| AU | 6189200 | 10/2001 | |
| CN | 102512706 | 6/2012 | |
| CN | 107670101 | 2/2018 | |
| EP | 2450064 | 5/2012 | |
| EP | 2450064 A1 * | 5/2012 | ......... A61L 24/0042 |
| HK | 1079464 | 12/2009 | |
| KR | 20150042660 | 4/2015 | |
| TW | 201726344 | 8/2017 | |
| TW | 201737950 | 11/2017 | |

OTHER PUBLICATIONS

Xu et al., "Self-hardening calcium phosphate cement-mesh composite: Reinforcement, macropores, and cell response", 2004, Journal of Biomedical Materials Research Part A, vol. 69, No. 2, pp. 267-278. (Year: 2004).*
Hsin-Wen Chen et al.,"Study of Calcium Sulfate and Calcium Phosphate Composite", Thesis of Institute of Materials Science and Engineering of National Taipei University of Technology,Jun. 2012, pp. 1-80.
"Office Action of Taiwan Counterpart Application", dated Nov. 9, 2018, p. 1-p. 3.
Kai-Chun Chang et al., "Development of calcium phosphate/sulfate biphasic cement for vital pulp therapy", Academy of Dental Materials. Published by Elsevier Ltd., Aug. 2014, pp. 362-370.
Man-Ping Chang et al., "A Feasibility Study Regarding the Potential Use of Silica-Doped Calcium Sulfate Anhydrite as a Bone Void Filler", Springer Berlin Heidelberg, Jun. 2017, pp. 879-886.

* cited by examiner

Primary Examiner — Michael B. Pallay
(74) Attorney, Agent, or Firm — JCIPRNET

(57) ABSTRACT

A method and a composite material used for free forming a bone substitute are provided. The composite material comprises a support cloth, and a partially hardened bone paste coated on the support cloth. The bone paste contains a mixture of calcium sulfate and calcium phosphate in a weight ratio of 1:1 to 1:4. The bone substitute can be made by laminating the composite material either on a bone model or not.

2 Claims, 8 Drawing Sheets

COMPOSITION MATERIAL AND METHOD FOR FREE FORMING BONE SUBSTITUTE

CROSS-REFERENCE TO RELATED APPLICATION

This application claims the priority benefit of the provisional application Ser. No. 62/470,897, filed on Mar. 14, 2017. The entirety of the above-mentioned patent application is hereby incorporated by reference herein and made a part of this specification.

BACKGROUND

1. Field of the Invention

This disclosure is related to a method and a composite material for free forming a bone substitute either by additive manufacturing or subtractive manufacturing, especially related to a method and a composite material for free forming a bone substitute.

2. Description of Related Art

Many shape-forming techniques are used for the fabrication of ceramic products. The most popular technique is a die-pressing technique which needs a steel mold. In the manufacturing process, the processed powder including ceramic powder mixed with binder and lubricant etc. is poured into the steel mold; then an external load is applied to press the powder together. Although the capability for mass production of the die-pressing is good, but the shape complexity thereof is quite limited. Furthermore, the cost of the steel mold for die-pressing is usually high. In order to produce a large quantity, a hard coating on the inner surface of the steel mold is usually needed, which can further push the cost of steel mold even higher.

In order to achieve shape complexity, an injection molding technique has also been used to fabricate ceramic article, but a large amount of additives, such as binder, plasticizer and surfactant, is needed to facilitate the injection molding. Moreover, the cost for the steel mold used for the injection molding is very high. Since a large amount of binder and plasticizer is used, the time needed to remove the additives through a de-binding process is very long, sometimes as long as days.

The demand on fast prototyping is increased due to the development of many personized products. For the development of new products, 5 to 10 prototypes may be more than enough for subsequent evaluation. If a mold is needed, the cost for the development of new products can be very high. Furthermore, to prepare a mold is also very time-consuming, and thus the development of new products can be slowed down.

In order to solve the problem, additive manufacturing process, such as 3D printing, has been developed recently. The additive manufacturing technique has achieved a great success for the fabrication of many plastic products. Almost any product with any shapes and any sizes can be made using the technique. The additive manufacturing technique has also been applied to metallic products through a selective laser sintering technique. However, it is not suitable for ceramic materials to use the similar additive methods above to produce ceramic articles. Therefore, an alternative on the prototyping of ceramic articles is needed, especially a highly customized forming method of a bone substitute is needed.

SUMMARY

Accordingly, in one aspect, a free forming method of a ceramic article is provided to achieve the prototyping of ceramic articles, such as a bone substitute. In this method, preferably, no adhesives or binders are needed.

According to one aspect, the method comprises the following steps. A first layer of bone paste is formed on a support cloth, wherein the bone paste is consisting essentially of a mixture of calcium sulfate and calcium phosphate. The bone paste is dried to form a partially hardened bone paste as an intermediate. The partially hardened bone paste is hardened by moisturizing the intermediate by an aqueous liquid and then drying to form a hardened bone paste.

In one embodiment, a weight ratio of the calcium sulfate and the calcium phosphate is 1:1 to 1:4.

In another embodiment, the calcium sulfate comprising $CaSO_4 \cdot 0.5H_2O$, $CaSO_4 \cdot 2H_2O$, or any combinations thereof; and the calcium phosphate is $Ca(H_2PO_4)_2$, $CaHPO_4$, $Ca_8(HPO_4)_2(PO_4)_4$, $Ca_3(PO_4)_2$, amorphous calcium phosphates, $Ca_{10-x}(HPO_4)_x(PO_4)_{6-x}(OH)_{2-x}$ ($0<x<1$), $Ca_{10}(PO_4)_6(OH)_2$, $Ca_{10}(PO_4)_6F_2$, $Ca_{10}(PO_4)_6O$, $Ca_4(PO_4)_2O$, or any combinations thereof.

In still another embodiment, the aqueous liquid is a buffer solution containing $Na_2H(PO_4)$ and $NaH_2(PO_4)_2$.

In still another embodiment, the hardened bone paste is sintered after the hardening step, so that the support cloth is removed and a porous bone ceramic is obtained.

In still another embodiment, the support cloth is weaved by a biodegradable fiber selected from a group consisting of polylactide, poly(lactic-co-glycolic acid), poly(propylene fumarate), and any combinations thereof.

In still another embodiment, the forming step and the drying step for several times between the drying step and the hardening step above, so that the intermediate has a laminated structure.

In still another embodiment, each layer of the bone paste in the intermediate is hardened according to identified cross-sectional patterns of a bone substitute in sequence to obtain a hardened bone substitute.

In still another embodiment, unrequired portions of the hardened bone paste of the intermediate are removed after the hardening step to form a hardened bone substitute.

In still another embodiment, the support cloth covers a model of the bone substitute before the forming step.

In still another embodiment, the forming step and the drying step are repeated for several times between the drying step and the hardening step, so that the intermediate has a laminated structure.

In another aspect, a composite material for free forming a bone substitute is also provided. The composite material comprises a support cloth and a layer of partially hardened bone past coated on the support cloth. The partially hardened bone past is consisting essentially of a mixture of calcium sulfate and calcium phosphate in a weight ratio of 1:1 to 1:4.

In still another aspect, a bone substitute is also provided. The material of the bone substitute comprises a hardened bone substitute material consisting essentially of calcium sulfate and calcium phosphate mixed by a weight ratio of 1:1 to 1:4, and channels distributed in the hardened bone substitute material.

In some embodiments, there are fibers in the channels.

DESCRIPTION OF THE EMBODIMENTS

Composite Material for Free Forming Ceramic Article and Preparation Method Thereof A composite material for free forming a ceramic article is provided. The composite material comprises a support cloth weaved by an organic fiber, and a partially hardened ceramic paste distributed on the support cloth. This composite material is used as an intermediate to prepare a ceramic article by free forming methods described below.

Figure 1A:
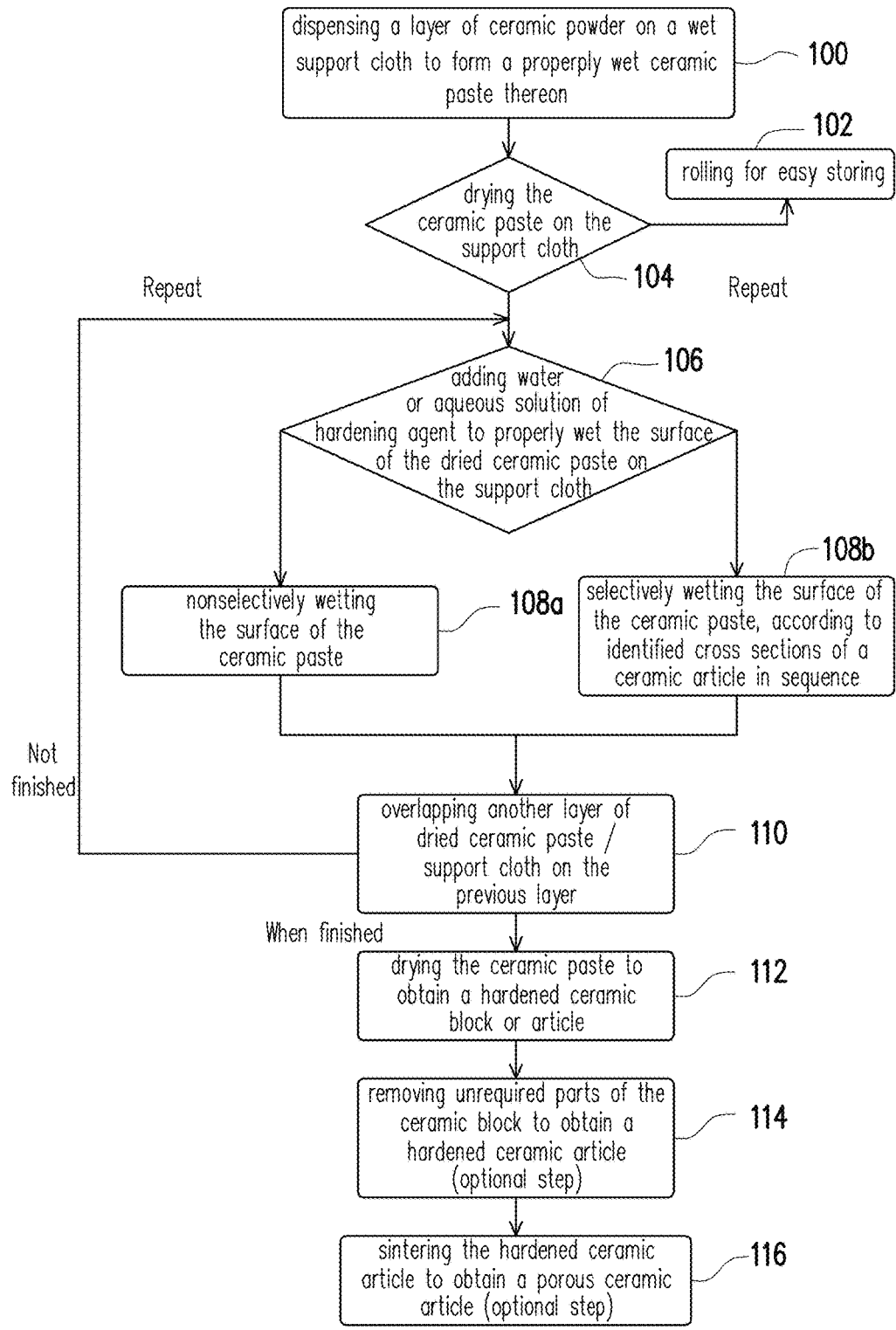
FIGS. 1A-1C are process flow diagrams showing free forming methods of ceramic articles.

The composite material may be prepared by dispensing dry ceramic powder on a wet support cloth, such as the steps 100-104 in the process flow diagram shown in FIG. 1A. After that, a drying step is performed to obtain the partially hardened ceramic paste on the support cloth. The ceramic powder and the support cloth usually is moisturized by water, so that the dried ceramic paste may be softened again by adding water or an aqueous solution to facilitate the shaping of the ceramic paste.

In some embodiment, the material of the initial ceramic powder above may be calcium sulfate, calcium phosphate, hydroxyapatite, calcium carbonate, calcium hydroxide, magnesium carbonate, strontium carbonate, kaolin, or a combination thereof. The ceramic paste above exhibits a self-setting capability; namely, the partially hardened ceramic paste can be hardened after mixing with an aqueous liquid, such as water or other aqueous solution containing a hardening agent.

The organic fiber may be made from poly(lactic acid) (PLA), poly(lactic-co-glycolic acid) (PLGA), poly(propylene fumarate) (PPF), polycaprolactone (PCL), polyethylene glycol (PEG), poly($\alpha$-hydroxy ester), poly(N-isopropyl acrylamide) (PNIPA), pluronic block copolymers, carboxymethyl cellulose (CMC), or any combinations thereof, for example. In some embodiments, the organic fiber is a biodegradable fiber, which may be made from PLA, PLGA, PPF, or any combinations thereof, for example.

Free Forming Method of Ceramic Article

Basic Method

In a basic method of free forming a ceramic article, the composite material above may be directly hardened by adding the aqueous liquid above. Then, unrequired parts may be removed by available subtractive means, such as cutting, drilling, or grinding.

Figure 1B:
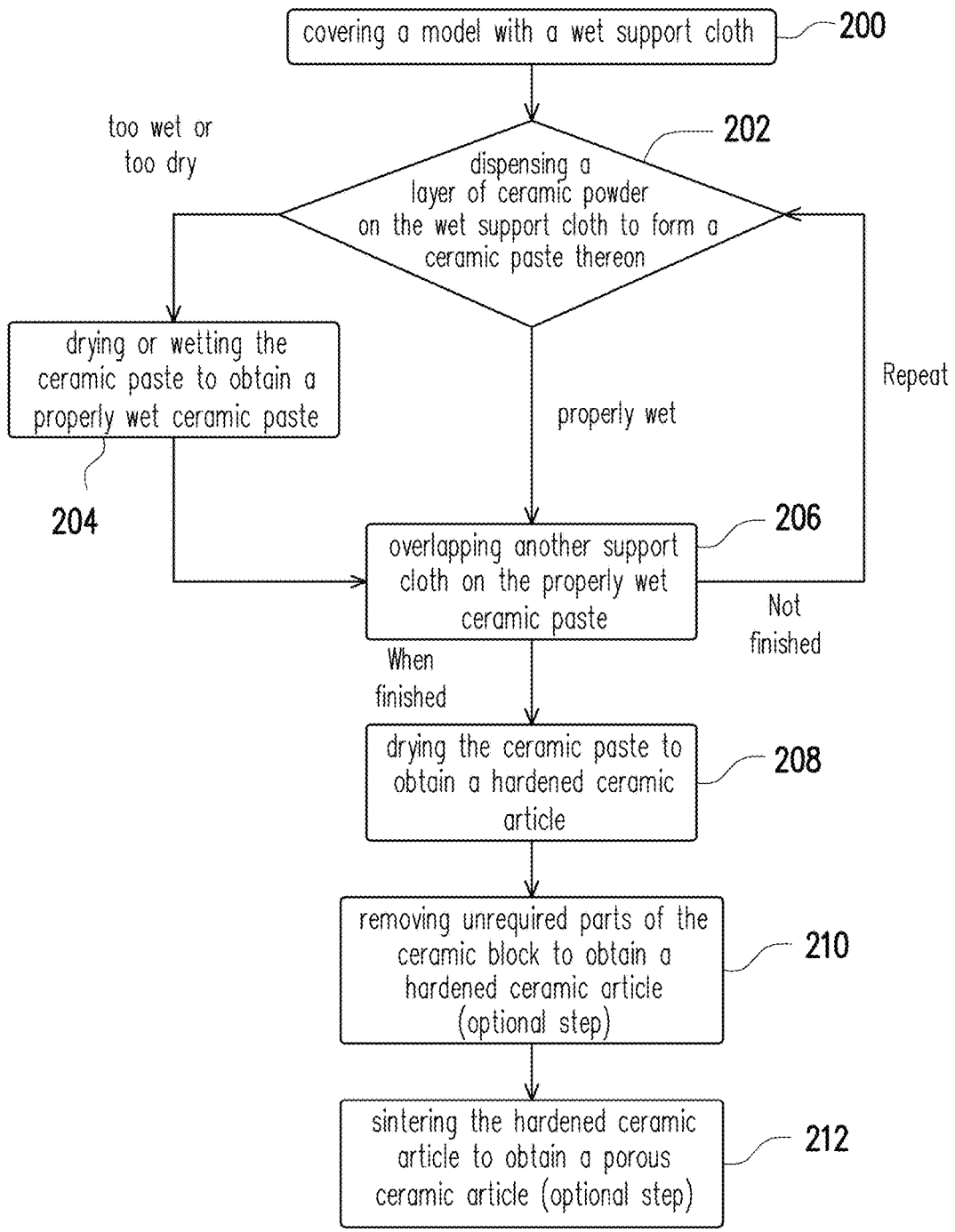

Moreover, in some embodiments, the support cloth may further cover a model of a desired ceramic article, such as a model having a shape of a needed bone substitute, so that the ceramic article may be directly obtained after the ceramic paste is hardened by the aqueous liquid. The details of the process flow, please see steps 200-212 in FIG. 1B.

The hardened ceramic articles above may be further sintered at a temperature above 600° C. to remove support cloth to form a porous ceramic article having channels left by the support cloth.

Subtractive Manufacturing Method

Please see FIG. 1A. In some embodiments, if the thickness of the hardened composite material above is not enough for the desired article, the moisturized composite material also may be stacked layer-by-layer to form an intermediate having a laminated structure before the hardening step, such as steps 106-110 in FIG. 1A. The number of the layers of the composite material in the laminated structure is determined by the needed thickness of the desired ceramic article.

After hardening the laminated structure in step 112 of FIG. 1A, unrequired parts may be removed by available subtractive means, such as cutting, drilling, or grinding, to form the desired ceramic article in the step 114 of FIG. 1A. Next, the processed laminated structure may be further sintered to form a porous ceramic article in the step 116 of FIG. 1A.

Figure 1C:
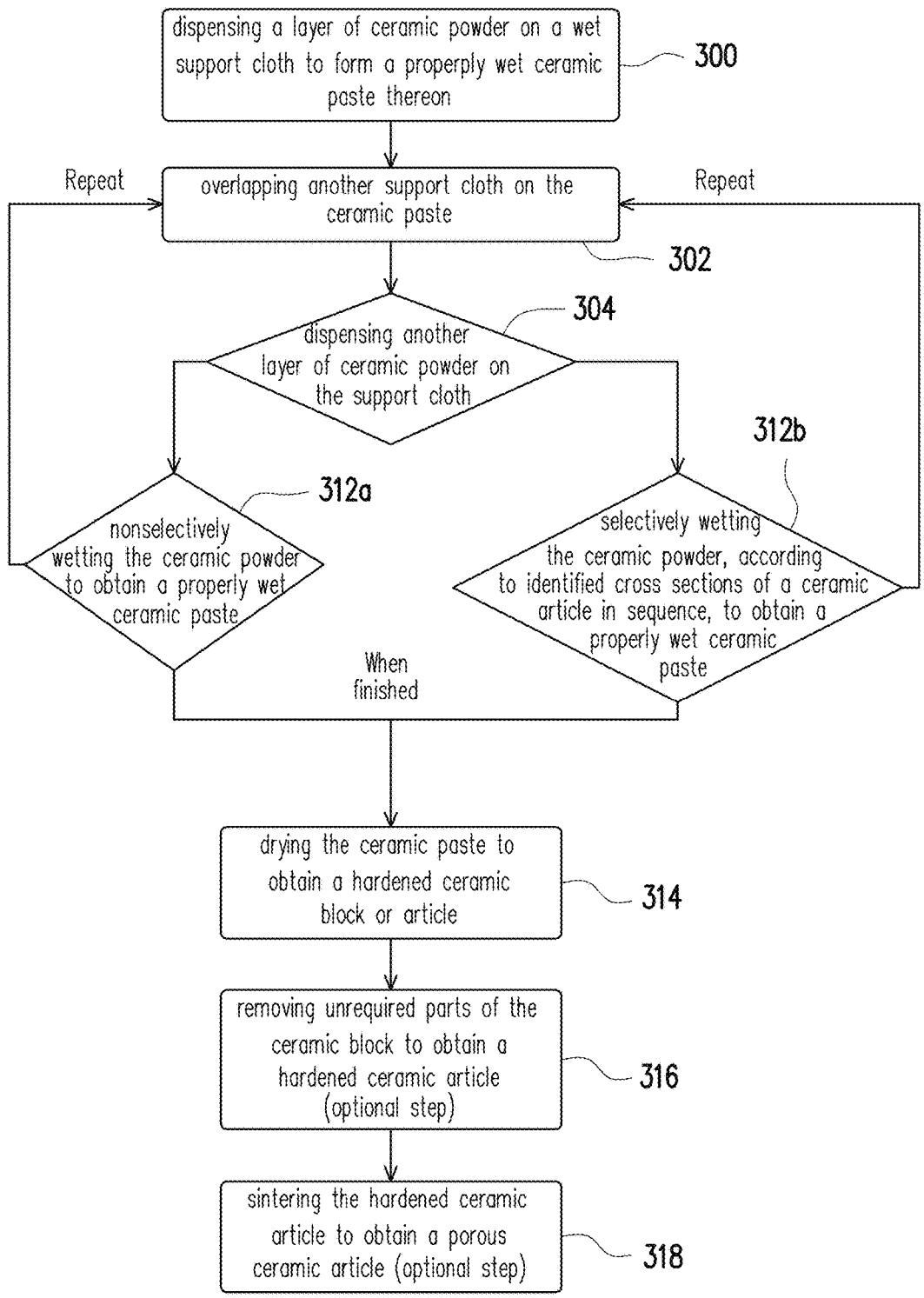

Please see FIG. 1C. The laminated structure may also be formed by repeatedly performing the steps 302-306a or 302-306b in FIG. 1C. The rest steps in FIG. 1C are similar to those corresponding steps in FIG. 1A, and hence the related descriptions are omitted here.

Additive Manufacturing Method

In some embodiments, the cross sections of a ceramic article are sequentially identified. Next, during the lamination process, each layer of the ceramic paste may be hardened according to identified cross-sections of a desired ceramic article in sequence, such as in step 108b in FIG. 1A and step 306b in FIG. 1C. That is, the hardening step in the basic method is performed by applying the aqueous liquid only on the identified cross sections on each layer. Therefore, after the lamination process (steps 106, 108b and 110 in FIG. 1A, or steps 302, 304 and 306b in FIG. 1C) and the removal of the non-hardened parts (step 114 in FIG. 1A, and step 310 in FIG. 1C), a hardened ceramic article may be obtained.

Forming Bone Substitute

When the ceramic article above is used as a bone substitute, the initial ceramic powder for preparing the ceramic paste above, i.e. a bone paste, may be a mixture of calcium sulfate and calcium phosphate, essentially. A weight ratio of the calcium sulfate and the calcium phosphate is 1:1 to 1:4.

In some other embodiments, the calcium sulfate is $CaSO_4 \cdot 0.5H_2O$, $CaSO_4 \cdot 2H_2O$, or any combinations thereof. In some other embodiments, anhydrous calcium sulfate may also be included. In yet some other embodiments, the calcium phosphate is $Ca(H_2PO_4)_2$, $CaHPO_4$, $Ca_8(HPO_4)_2(PO_4)_4$, $Ca_3(PO_4)_2$, amorphous calcium phosphates, $Ca_{10-x}(HPO_4)_x(PO_4)_{6-x}(OH)_{2-x}$ (0<x<1), $Ca_{10}(PO_4)_6(OH)_2$, $Ca_{10}(PO_4)_6F_2$, $Ca_{10}(PO_4)_6O$, $Ca_4(PO_4)_2O$, or any combinations thereof. The calcium sulfate is used to adjust the hardening rate of the ceramic paste.

Furthermore, the aqueous liquid above used to harden the bone paste is water or a buffer solution of sodium hydrogen phosphate ($Na_1H(PO_4)/NaH_2(PO_4)_2$). The concentration of the sodium hydrogen phosphate in the buffer solution may be 0.1-1 M. Generally, the higher the concentration is, the faster the hardening rate is.

When a bone substitute is needed to be implanted into a body, a hardened bone substitute or a sintered bone substitute may be used. If a hardened bone substitute, rather than a sintered bone substitute is used, the support cloth should be woven by a biodegradable fiber. If a sintered bone substitute is used, there is no limitation of the fiber used to weave the support cloth.

Moreover, a composite material having a partially hardened bone paste on a support cloth also may be used as an implant, since the partially hardened bone paste may be hardened after contacting the tissue liquid surrounding the implanted site.

The detailed explanations and examples for the ceramic powder/paste, the support cloth, and the moisturizing liquid have been illustrated above, and thus is not repeated here.

Example 1: Preparing a $CaSO_4.2H_2O$ Powder/Fiber Cloth Composite

Figure 2A:
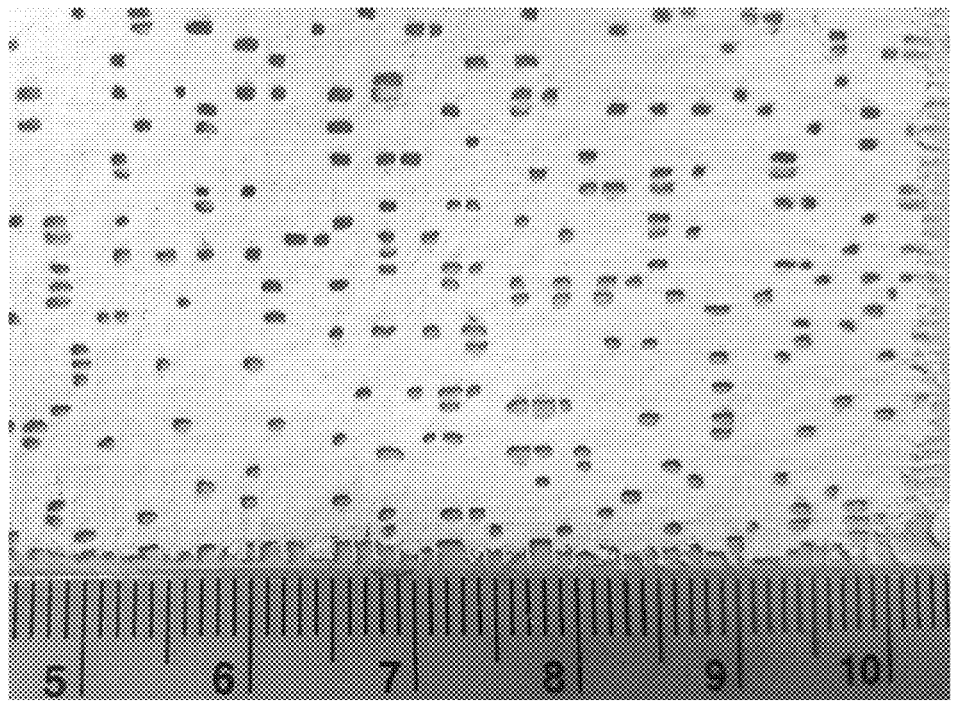
FIG. 2A is a photograph showing a morphology of the composite material of $CaSO_4 \cdot 2H_2O$ powder/fiber cloth.

In this example, the ceramic used was $CaSO_4.2H_2O$ powder, and the fiber cloth was a cotton cloth weaved by cotton fibers having a diameter of about 100 µm. The distance between two fibers is about 1,000 µm. The composite material may be prepared by moisturizing the $CaSO_4.2H_2O$ powder by a small amount of water, and then coating the wet $CaSO_4.2H_2O$ powder onto the fiber cloth. The composite material may also be prepared by soaking the fiber cloth with water, and then attaching the $CaSO_4.2H_2O$ powder on to the wet cotton cloth. FIG. 2A is a photograph showing a morphology of the composite material of $CaSO_4.2H_2O$ powder/fiber cloth.

Figure 2B:
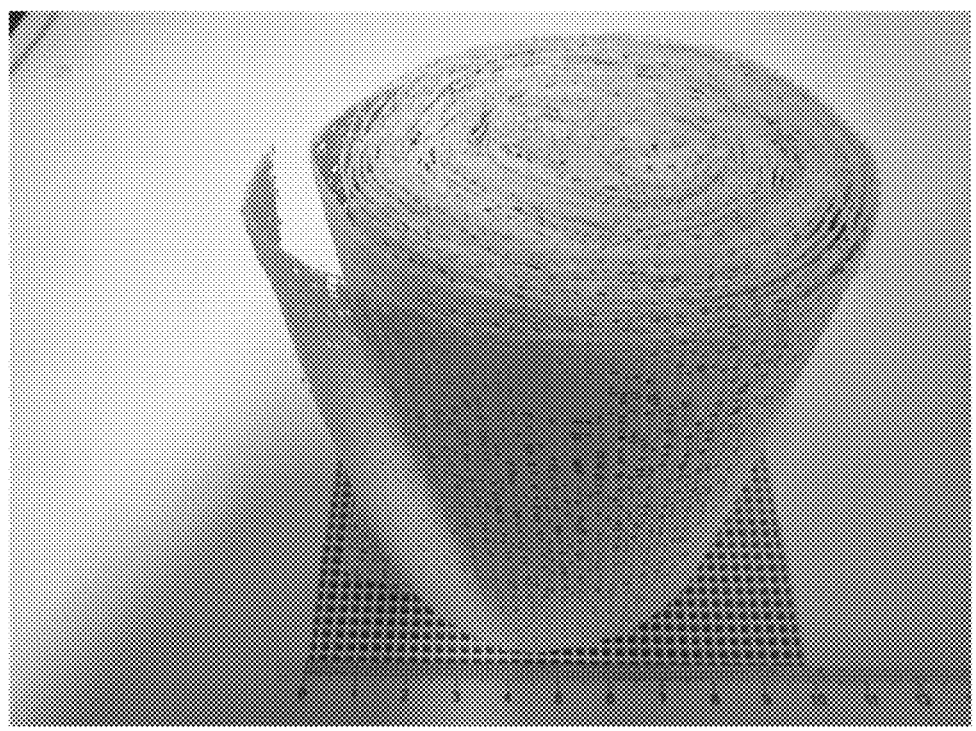
FIG. 2B is a photograph showing a roll of the dried composite material of $CaSO_4 \cdot 2H_2O$ powder/fiber cloth.

Finally, the wet composite material is dried in air. FIG. 2B is a photograph showing a roll of the dried composite material of $CaSO_4.2H_2O$ powder/fiber cloth. In FIG. 2B, it can be seen that the dried composite material is still flexible, so that a roll of the dried composite material may be formed for easy deposition.

Example 2: Forming a Ceramic Block of $CaSO_4.2H_2O$ Powder/Fiber Cloth Composite In this example, the $CaSO_4.2H_2O$ powder/fiber cloth composite material of Example 1 was stacked layer by layer to form a ceramic block. First, a first layer of the composite material was hardened by miniaturization with water. Next, a second composite layer is stacked on the first layer and then moisturized. The steps above are repeated until a desired thickness of the stacked composite material is reached. Subsequently, the stacked composite material is dried. For example, the drying temperature may be 60° C. or above to speed the drying process.

Figure 3A:
FIG. 3A is a photograph showing a piece of ceramic plate after laminating 6 layers of $CaSO_4 \cdot 2H_2O$ powder/fiber cloth composite material.

FIG. 3A is a photograph showing a piece of ceramic plate after laminating 6 layers of $CaSO_4.2H_2O$ powder/fiber cloth composite material. The self-hardening process takes only several minutes. An external heating source can shorten the time needed for drying. After grinding the edge of the specimens, the size of green plate was 73 mm (length)×28 mm (width)×5.5 mm (thickness). The strength of green plate was measured with a three-point bending technique with a universal testing machine. The loading rate was 1 mm/min. The average value for the 3-point bending strength of the green plate was 5.6±0.85 MPa, and the number of the tested samples is at least three.

Figure 3B:
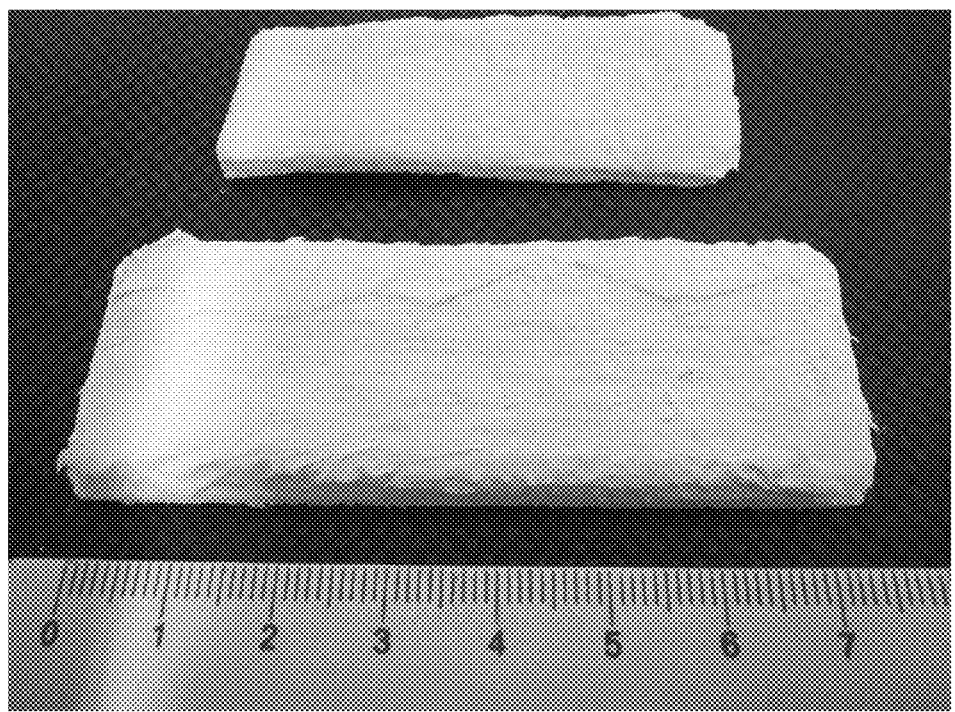
FIG. 3B is a photograph showing the morphology of the specimens before (the specimen in the front) and after sintering (the specimen at the back).
Figure 3C:
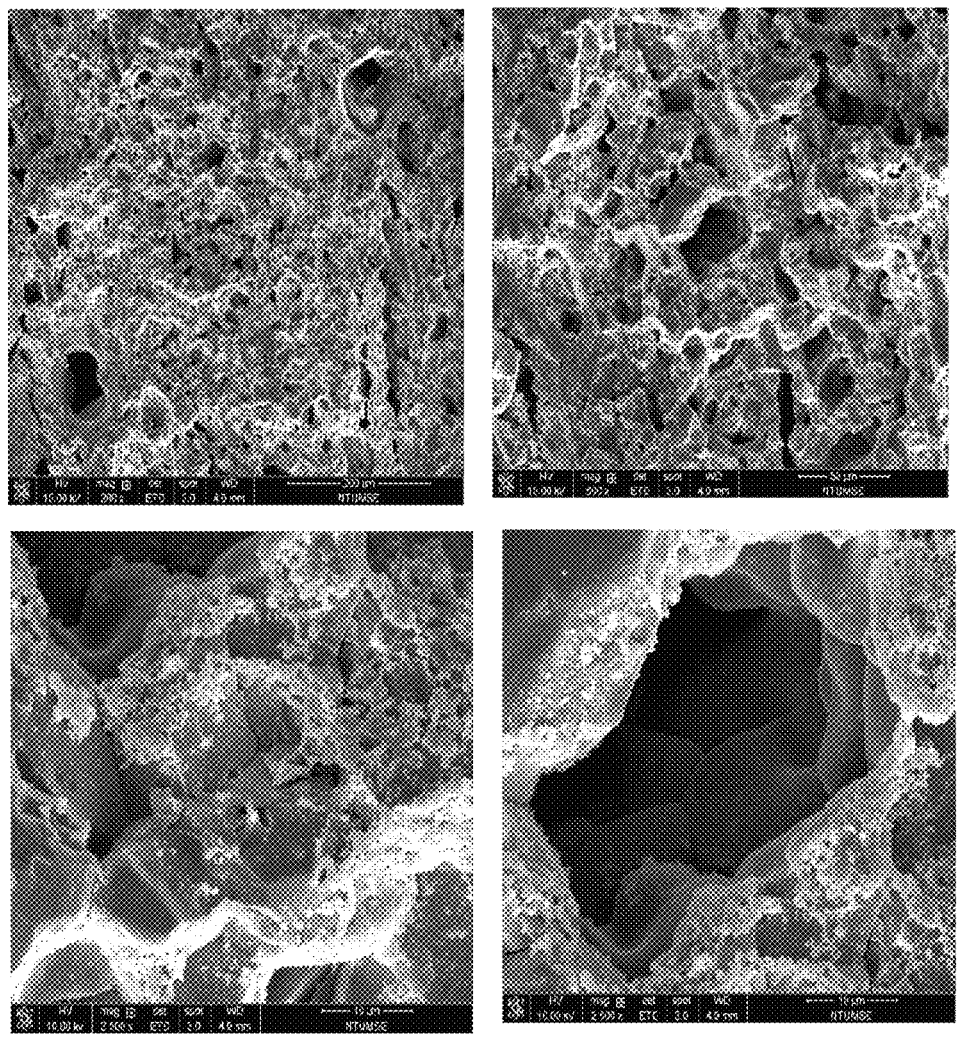
FIG. 3C shows photographs showing the fracture surface of the specimen after sintering.

The specimens were then sintered in a furnace. The fiber was burned away at a temperature of 600° C. Then the densification of the plate is carried out at a sintering temperature of 1050° C. The dwell time at the temperature is 1 hour. FIG. 3B is a photograph showing the morphology of the specimens before and after sintering. The length of the plate has been decreased by 15%, indicating that the density of the ceramic plate was increased using the sintering technique. The 3-point bending strength was then measured. The average value for the bending strength was 1.6 MPa, and the number of the tested samples is at least three. FIG. 2C shows photographs showing the fracture surface of the specimen after sintering. Continuous pores were formed after burning away the fiber. The calcium sulfate grains could be observed, along with the pores.

Example 3: Preparing a Head of Humerus by Using $CaSO_4.2H_2O$ Powder/Fiber Cloth Composite For the preparation of ceramic head of humerus, a plastic head of humerus is used first. The plastic head is then covered with the ceramic/organic-fiber composite layer by layer, using the method in Example 2. Namely, two to three composite layers are applied onto the plastic body with the help of a small amount of water. Shear stresses are also applied at the same time. The head of humerus can then be prepared. Next, the plastic body may be removed by melting or thermal decomposition.

Figure 4:
FIG. 4 is a photograph showing a piece of humerus head before sintering prepared in Example 3.

In this example, the plastic head also can be replaced by wax head in the begging. The wax head was removed at a temperature above 300° C. FIG. 4 is a photograph showing a piece of humerus head, prepared in Example 3, after drying. This specimen demonstrates that the ceramic with complex shape can be prepared using the sheet laminating technique, one of the additive manufacturing techniques.

Figure 5:
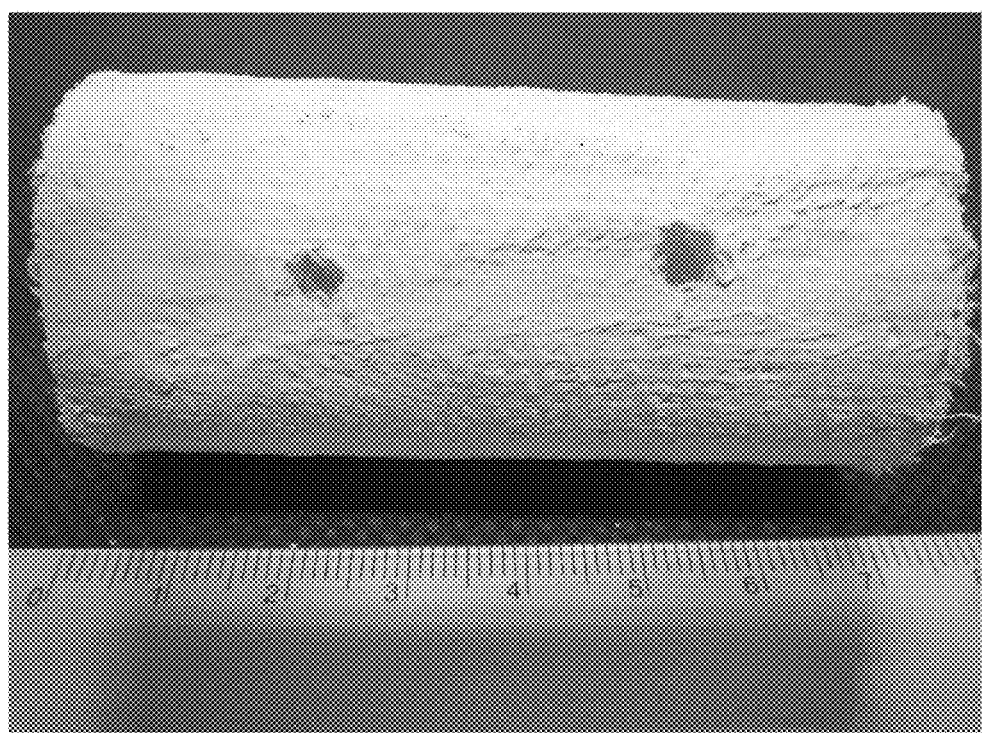
FIG. 5 is a photograph showing a green ceramic tube after cutting and drilling.

Example 4: Preparing a Ceramic Tube by Using $CaSO_4.2H_2O$ Powder/Fiber Cloth Composite The laminating of the ceramic/organic-fiber composite can also be used to prepare a ceramic tube. A tube with a length longer than 1000 mm and a diameter larger than 35 mm can be prepared. The subtractive manufacturing techniques, such as drilling, sawing and grinding etc., can all be used. The use of these techniques allows the preparation of any ceramic products with any complex shape. For example, FIG. 5 shows a green ceramic tube after cutting and drilling.

Example 5: Self-Hardening Test for the Ceramic Paste

The ceramic paste used and the results of the self-hardening test are listed in Table 1 below.

TABLE 1

| Self-hardening test | | | |
| --- | --- | --- | --- |
| ceramics | powder weight | water volume | self-hardening time |
| $CaSO_4 \cdot 2H_2O$ | 5.0 g | 4.0 mL | >5 minutes |
| $CaSO_4 \cdot 0.5H_2O$ | 5.0 g | 4.0 mL | 1 hour |
| $CaSO_4 \cdot 0.5H_2O:Ca_3(PO_4)_2$ | 0.4 g:1.6 g | 2.2 mL | 1 hour |
| $CaSO_4 \cdot 0.5H_2O:Ca_3(PO_4)_2$ | 1.6 g:1.3 g | 2.4 mL | 1 hour |
| $Ca_3(PO_4)_2$ | 2.5 g | 2.0 mL | 3 days |

As demonstrated in the above, calcium sulfate dihydrate ($CaSO_4 2H_2O$), calcium sulfate hemihydrate ($CaSO_4$ $0.5H_2O$), tricalcium phosphate ($Ca_3(PO_4)_2$) and a mixture comprising one or more of the above powders, can be used as the ceramic paste for the ceramic/organic-fiber composite. The ceramic paste can mix with the organic fiber to form the composite. The additive manufacturing and subtractive manufacturing can all be used to prepare ceramic article with complex shape. Only water is needed to spray on the composite. The self-hardening can take place within several minutes to several days. As the time is as short as several minutes, the ceramic/organic-fiber composite can be used for the purpose of fast prototyping.

Example 6: Measuring Biaxial Strength of Sintered Ceramic Disc

Ceramic paste was die-pressed to form a cylindrical disc and then sintered. The sintered disc had a diameter of about 20 mm and a thickness of about 3 mm. The densities of the sintered discs were measured by the geometrical weight-volume method. The biaxial strengths of the sintered discs were measured with a biaxial loading fixture, and a one-ball-on-three-balls fixture. The probability of failure is also calculated by the equation (1).

Probability of failure=[$n_{th}$/(total number of specimens+0.5)]  (1)

Figure 6:
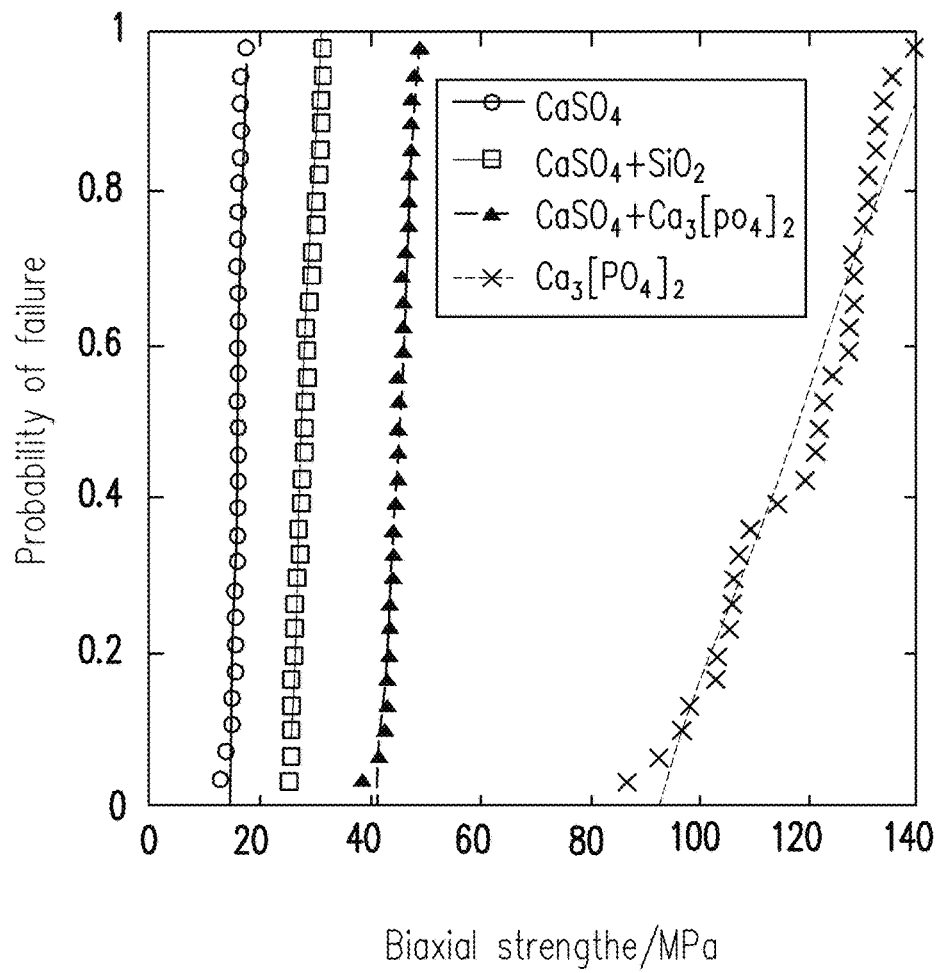
FIG. 6 is a diagram showing the curves of the probability of failure versus biaxial strength of the tested samples.

The $n_{th}$ is the sequence of the strength value as the strength values are ranked from low to high (W. H. Tuan, M J. Lai, M. C. Lin, C. C. Chan and S. C. Chiu, "The mechanical performance of alumina as a function of grain size", Mater. Chemistry and Physics, 36(3-4), 246-251 (1994)). The tested ceramics and the results of the biaxial strengths are listed in the Table 2 below. The curves of the probability of failure versus biaxial strength are shown in FIG. 6.

TABLE 2

Measurement of biaxial strength

| Ceramics | Sintering Temp (° C.) | Relative density (%) | Biaxial strength (MPa) | Number of discs tested |
|---|---|---|---|---|
| $CaSO_4$ | 1100 | 96 | 15.7 ± 0.8 | 28 |
| $^a CaSO_4 + SiO_2$ | 1100 | 95 | 28.1 ± 1.9 | 30 |
| $^b CaSO_4 + Ca_3(PO_4)_2$ | 1150 | 96.5 | 45 ± 2 | 30 |
| $^c CaSO_4 + Ca_3(PO_4)_2$ | 1150 | 96 | 108 ± 24 | 14 |
| $Ca_3(PO_4)_2$ | 1150 | 83.9 | 118 ± 14 | 30 |

$^a CaSO_4:SiO_2$ = 99:1 by weight.
$^b CaSO_4:Ca_3(PO_4)_2$ = 1:1 by weight.
$^c CaSO_4:Ca_3(PO_4)_2$ = 1:4 by weight.

Generally, the greater the biaxial strength is, the better the specimen to resist the external load is. Therefore, it can be seen that $Ca_3(PO_4)_2$ had the greatest biaxial strength among the tested samples. It means that the $Ca_3(PO_4)_2$ had the best mechanical strength among the tested samples. However, according to FIG. 6, the strength values of the mixture of $CaSO_4$ and $Ca_3(PO_4)_2$ exhibited a less extent on their scatter. It means that the reliability of the mixture of $CaSO_4$ and $Ca_3(PO_4)_2$ is better than $Ca_3(PO_4)_2$ alone. Therefore, the addition of $CaSO_4$ into $Ca_3(PO_4)_2$ not only can decrease the self-hardening time, but also can improve the reliability. At the same time, the biaxial strength of the $CaSO_4$ is increased by the addition of $Ca_3(PO_4)_2$. Hence, the mixture of $CaSO_4$ and $Ca_3(PO_4)_2$ is very suitable to be the material of a bone substitute.

Therefore, comparing with the conventional bone cement and bone substitute etc., the advantages of using the mixture of $CaSO_4$ and $Ca_3(PO_4)_2$ supported on a biodegradable fiber cloth (abbreviate as bone substitute composite below) in this disclosure includes:

1. The materials of the bone substitute composite in this disclosure are either bioabsorbable or biodegradable, and hence no second surgery is needed.

2. The self-hardening process is an exothermic reaction. The temperature of the composite material of the bone substitute may reach a temperature about 42-46° C. during setting. This temperature is lower than the temperature of the commercial bone cement using poly(methyl methacrylate) (PMMA) and a curing agent thereof as the adhesive or binder (about 70-80° C.). Therefore, the tissue surrounding the implanted site of the bone substitute will not be heavily injured by the heat released in the self-hardening process.

3. No adhesives or binders are needed in the composite material of the bone substitute in this disclosure, only an aqueous liquid is needed to set the ceramic paste.

4. The composite material can be used to prepare a ceramic article by either a subtractive manufacturing method or an additive manufacturing method.

What is claimed is:

1. A composite material for free forming a bone substitute, wherein the composite material comprises a first composite material unit and a second composite material unit stacked on the first composite material unit, and the first composite material unit and the second composite unit respectively comprises:
   a support cloth; and
   a layer of partially hardened bone paste coated on the support cloth, wherein the partially hardened bone paste is consisting essentially of a mixture of calcium sulfate and calcium phosphate in a weight ratio of 1:1 to 1:4,
   wherein the partially hardened bone paste of the first composite material unit is sandwiched between the support cloth of the first composite material unit and the support cloth of the second composite material unit.

2. The composite material of claim 1, wherein
   the calcium sulfate comprising $CaSO_4.0.5H_2O$, $CaSO_4.2H_2O$, or any combinations thereof; and
   the calcium phosphate is $Ca(H_2PO_4)_2$, $CaHPO_4$, $Ca_8(HPO_4)_2(PO_4)_4$, $Ca_3(PO_4)_2$, amorphous calcium phosphates, $Ca_{10-x}(HPO_4)_x(PO_4)_{6-x}(OH)_2$, ($0<x<1$), $Ca_{10}(PO_4)_6(OH)_2$, $Ca_{10}(PO_4)_6F_2$, $Ca_{10}(PO_4)_6O$, $Ca_4(PO_4)_2O$, or any combinations thereof.

* * * * *